US006261775B1

(12) United States Patent
Bastian et al.

(10) Patent No.: US 6,261,775 B1
(45) Date of Patent: Jul. 17, 2001

(54) DETECTION OF CHROMOSOME COPY NUMBER CHANGES TO DISTINGUISH MELANOCYTIC NEVI FROM MALIGNANT MELANOMA

(75) Inventors: Boris Bastian, San Francisco; Daniel Pinkel, Walnut Creek, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/288,940

(22) Filed: Apr. 9, 1999

(51) Int. Cl.[7] ................................................. C12Q 1/68
(52) U.S. Cl. ................................................................ 435/6
(58) Field of Search ..................................................... 435/6

(56) References Cited

PUBLICATIONS

Wettengel et al "Differentiation between Spitz nevi and malignant melanomas by interphase Fish", Int. J. of Oncology, vol. 14, pp. 1177–1183, 1999.*
De Witt et al "DNA in situ Hybridization as a Diagnostic tool in the discrimination of melanoma and spitz naevus" J. of Pathology, vol. 173, pp. 227–233, 1994.*
Bastian et al. "Chromosomal Gains and Losses in Primary Cutaneous Melanomas Detected by CGH" Cancer Research, vol. 58, pp. 2170–2175, May 1998.*
Healy et al. "Allelotypes of Primary Cutaneous Melanoma and Benign Melanocytic Nevi" Cancer Research, vol. 56, pp. 589–593, Feb. 1996.*
Lichter et al. "Delinieation of individual human chromosomes in metaphase and interphase cells by in situ suppression hybridization using recombinant DNA libraries" Hum Genet. vol. 80, pp. 224–234, 1988.*
Matson et al. "Biopolymer Synthesis on Polypropylene Supporst: Oligonucleotide Arrays" Analytical Biochemistry, vol. 224, pp. 110–116, 1995.*
Wang et al. "COT–1 banding of human chromosomes using Fish with Cy3 labeling" Jpn. J. Human Genet. vol. 40, pp. 243–252, 1995.*
Thompson et al., *Cancer Genet. Cytogent.* (1995) 83: 93–104 Get—Listed In Spec.
Winokur et al. *J. Cutan Pathol.* (1990) 17: 342–347 Get—Listed As #(10) In Spec, In Manuscript?

* cited by examiner

*Primary Examiner*—Lisa B. Arthur
*Assistant Examiner*—Jeanine Goldberg
(74) *Attorney, Agent, or Firm*—Townsend and Townsend and Crew LLP

(57) ABSTRACT

The present invention provides for methods of distinguishing melanocytic nevi, such as Spitz nevi, from malignant melanoma. The methods comprise contacting a nucleic acid sample from a patient with a probe which binds selectively to a target polynucleotide sequence on a chromosomal region such as 11p, which is usually amplified in Spitz nevi. The nucleic acid sample is typically from skin tumor cells located within a tumor lesion on the skin of the patient. Using another probe which binds selectively to a chromosomal region such as 1q, 6p, 7p, 9p, or 10q, which usually show altered copy number in melanoma, the method can determine that those tumor cells with no changes in copy number of 1q, 6p, 7p, 9p, or 10q, are not melanoma cells but rather Spitz nevus cells. The finding of amplifications of chromosome 11p would be an additional indication of Spitz nevus.

18 Claims, 4 Drawing Sheets

DETECTION OF CHROMOSOME COPY NUMBER CHANGES TO DISTINGUISH MELANOCYTIC NEVI FROM MALIGNANT MELANOMA

BACKGROUND OF THE INVENTION

The melanocyte can give rise to a plethora of morphologically different tumors. Most of them are biologically benign and are referred to as melanocytic nevi. Examples of melanocytic nevi are congenital nevi, Spitz nevi, dysplastic or Clark's nevi, blue nevi, lentigo simplex, and deep penetrating nevus. Pigmented spindle cell nevus is regarded as a subset of Spitz nevi.

Spitz nevi are benign melanocytic neoplasms that can have considerable histological resemblance to melanoma. They were first described as "juvenile melanoma" by Sophie Spitz in 1948 and initially regarded as a subset of childhood melanoma that follows a benign course (Spitz, S., Am. J. Pathol. 24, 591–609 (1948)). Spitz nevi are common and account for about 1% of surgically removed nevi (Casso et al., J Am Acad Dermatol., 27, 901–13 (1992)). Although in general the pathological diagnosis of Spitz nevus is straightforward, there is a subset of cases in which it is difficult to impossible to differentiate Spitz nevi from melanoma. The diagnostic difficulties are explained by overlapping histological features. Both Spitz nevi and melanoma can be composed of melanocytes with abundant cytoplasm and large nuclei. Nuclei can be pleomorphic and contain macronucleoli. Mitotic figures, sometimes numerous, occur in both neoplasms.

Melanoma refers to malignant neoplasms of melanocytes. Its proper diagnosis and early treatment is of great importance because advanced melanoma has a poor prognosis, but most melanomas are curable if excised in their early stages. While clinicians make the initial diagnosis of pigmented lesions of the skin, pathologists make the final diagnosis. Although, in general the histopathological diagnosis of melanoma is straightforward, there is a subset of cases in that it is difficult to differentiate melanomas from benign neoplasm of melanocytes, which have many variants that share some features of melanomas (LeBoit, P. E. STIMULANTS OF MALIGNANT MELANOMA: A ROGUE'S GALLERY OF MELANOCYTIC AND NON-MELANOCYTIC IMPOSTERS, In *Malignant Melanoma and Melanocytic Neoplasms*, P. E. Leboit, ed. (Philadelphia: Hanley & Belfus), pp. 195–258 (1994)). Even though the diagnostic criteria for separating the many simulators of melanoma are constantly refined, a subset of cases remains, where an unambiguous diagnosis cannot be reached (Farmer et al., DISCORDANCE IN THE HISTOPATHOLOGIC DIAGNOSIS OF MELANOMA AND MELANOCYTIC NEVI BETWEEN EXPERT PATHOLOGISTS, Human Pathol. 27: 528–31 (1996)). The most frequent and important diagnostic dilemma is the differential diagnosis between Spitz nevus, a neoplasm composed of large epithelioid or spindled melanocytes, and melanoma.

Misdiagnosis of Spitz nevus as melanoma and vice versa has been repeatedly reported in the literature (Goldes et al., Pediatr. Dermatol., 1: 295–8 (1984); Okun, M. R. Arch. Dermatol. 115: 1416–1420 (1979); Peters et al., Histopathology, 10, 1289–1302 (1986)). A retrospective study of 102 melanomas of childhood found that only 60 cases were classified as melanoma by a panel of experts, the majority of the remainder being classified as Spitz nevi (Spatz, S., Int. J. Cancer 68, 317–24 (1996)). The hazard of mistaking a Spitz nevus for melanoma can be severe and traumatic: The patients may be subjected to needless surgery, unable to plan for the future, and psychologically traumatized. For obvious reasons, the misdiagnosis of a melanoma as a benign nevus can have even more dramatic consequences. The presence of this diagnostic gray zone has even led the authors of a review article in the "Continuing Medical Education" section of the *Journal of the American Association of Dermatology* to conclude that Spitz nevus and melanoma may "actually exist on a continuum of disease" (Casso et al., J. Am. Acad. Dermatol., 27, 901–13 (1992)). The authors recommended that "treatment include complete excision of al Spitz nevi followed by reexcision of positive margins if present." The need for improved diagnostics for melanocytic neoplasms has led to numerous attempts to improve diagnostic accuracy by the use of markers that could be detected by immuno-histochemistry. While there have been prior efforts aimed at resolving this problem, none have been satisfactory. For example, even though tests employing markers such as S 100, HMB45 are useful in establishing that a poorly differentiated tumor is of melanocytic lineage, adjunctive techniques have been of little help in separating benign from malignant melanocytic lesions.

Thus, there exists a great need for improved and accurate diagnostic methods to distinguish Spitz nevi from malignant melanoma. The present invention addresses these and other needs.

SUMMARY OF THE INVENTION

The present invention provides for methods of distinguishing melanocytic nevi, such as Spitz nevi, from malignant melanoma. The methods comprise detecting a target polynucleotide sequence on a chromosomal region such as 11p, particularly 11p15.5, which is usually amplified in Spitz nevi. The nucleic acid sample is typically taken from skin tumor tissue located within a tumor lesion on the skin of the patient. The methods can also be used to determine whether the tumor cells lack changes in chromosomal regions associated with melanoma (e.g., 1q, 6p, 7p, or 10q). Usually, the copy number of the target region is measured.

The nucleic acid sample can be extracted from an interphase nucleus. Typically, the probe is labeled e.g. with a fluorescent label. The label may be a direct label. Usually, a reference probe to a second chromosomal region is used in the methods as an internal control. In these embodiments, the second probe is labeled with a fluorescent label distinguishable from the label on the probe that selectively hybridizes to the target polynucleotide sequence.

In some embodiments, the probe may include repetitive sequences. In this case, the methods may further comprising the step of blocking the hybridization capacity of repetitive sequences the probe Unlabeled blocking nucleic acids comprising repetitive sequences (e.g. Cot-1 DNA) can be contacted with the sample for this purpose.

The nucleic acid hybridization can be carried out in a number of formats. For instance, the hybridization may be an in situ hybridization. In some embodiments, the probe is bound to a solid substrate, e.g. as a member of a nucleic acid array.

Definitions

To facilitate understanding the invention, a number of terms are defined below.

The terms "melanoma" or "cutaneous melanoma" refer to malignant neoplasms of melanocytes, which are pigment cells present normally in the epidermis and sometimes in the dermis. There are four types of cutaneous melanoma: lentigo maligna melanoma, superficial spreading melanoma (SSM), nodular melanoma, and acral lentiginous melanoma (AM). Melanoma usually starts as a proliferation of single melanocytes at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

The terms "Spitz nevi" or "Spitz nevus" refer to benign melanocytic neoplasms that can have considerable histological resemblance to melanoma. They were first described as "juvenile melanoma" and initially were thought of as a subset of childhood melanoma that follows a benign course. Spitz nevi are common and account for about 1% of surgically removed nevi.

The terms "tumor" or "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may be a non-tumorigenic cancer cell, such as a leukemia cell. Cancers include, but are not limited to melanomas, breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, chondrosarcoma, and the like.

The phrase "detecting a tumor or a cancer" refers to the ascertainment of the presence or absence of cancer in an animal, in this case, melanoma cells or premalignant melanocytes. "Detecting a tumor or a cancer" can also refer to obtaining indirect evidence regarding the likelihood of the presence of cancerous cells in the animal or to the likelihood of predilection to development of a cancer. Detecting a cancer can be accomplished using the methods of this invention alone, or in combination with other methods or in light of other information regarding the state of health of the animal.

The term "animal" refers to a member of the kingdom Animalia, characterized by multicellularity, the possession of a nervous system, voluntary movement, internal digestion, etc. An "animal" can be a human or other mammal. Preferred animals include humans, non-human primates, and other mammals. Thus, it will be recognized that the methods of this invention contemplate veterinary applications as well as medical applications directed to humans.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology— Hybridization with Nucleic Acid Probes part I, Ch. 2, "Overview of principles of hybridization and the strategy of nucleic acid probe assays,"* Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1–3, Cold Spring Harbor Laboratory, Cold Spring Harbor Press, N.Y., and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

The term "labeled with a detectable composition", as used herein, refers to nucleic acid attached to a detectable composition, i.e., a label. The detection can be by, e.g., spectroscopic, photochemical, biochemical, immunochemical, physical or chemical means. For example, useful labels include $^{32}P$, $^{35}S$, $^{3}H$, $^{14}C$, $^{125}I$, $^{131}I$; fluorescent dyes (e.g., FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g Dynabeads™), biotin, digoxigenin, or haptens and proteins for which antisera or monoclonal antibodies are available. The label can be directly incorporated into the nucleic acid, peptide or other target compound to be detected, or it can be attached to a probe or antibody that hybridizes or binds to the target. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., *Mansfield, Mol Cell Probes* 9: 145–156 (1995). In addition, target DNA sequences can be detected by means of the primed in situ labeling technique (PRINS) (Koch et al., *Genet. Anal. Tech. Appl.* 8: 171–8, (1991)). The sensitivity of the detection can be increased by using chemical amplification procedures using e.g. tyramide (Speel et al., *J. Histochem. Cytochem.* 45:1439–46, (1997)).

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/0321 1; WO 96/39154; Mata (1997) *Toxicol. AppL. Pharmacol.* 144:189–197. Other synthetic backbones encompasses by the term include methylphosphonate linkages or alternating methylphosphonate and phosphodiester linkages (Strauss-Soukup (1997) *Biochemistry* 36: 8692–8698), and benzylphosphonate linkages (Samstag (1996) *Antisense Nucleic Acid Drug Dev* 6: 153–156). The term nucleic acid is used interchangeably with gene, cDNA, mRNA, oligonucleotide primer, probe and amplification product.

The term a "nucleic acid array" as used herein is a plurality of target elements, each target element comprising one or more nucleic acid molecules (probes) immobilized on one or more solid surfaces to which sample nucleic acids can be hybridized. The nucleic acids of a target element can contain sequence(s) from specific genes or clones, e.g. from the regions identified here. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 $\mu$m to about 3 mm, preferably between about 5 $\mu$m and about 1 mm. The target elements of the arrays may be arranged on the solid surface at different densities. The target element densities will depend upon a number of factors, such as the nature of the label, the solid support, and the like. One of skill will recognize that each target element may comprise a mixture of nucleic acids of different lengths and sequences. Thus, for example, a target element may contain more than one copy of a cloned piece of DNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations. In various embodiments, target element sequences will have a complexity between about 1 kb and about 1 Mb, between about 10 kb to about 500 kb, between about 200 to about 500 kb, and from about 50 kb to about 150 kb.

The terms "nucleic acid sample" or "sample of human nucleic acid" as used herein refers to a sample comprising human DNA or RNA in a form suitable for detection by hybridization or amplification. Typically, it will be prepared from a skin tissue sample from a patient who has or is suspected of having melanocytic tumor that may be difficult to classify. The sample will most usually be prepared from tissue taken from the tumor.

In many instances, the nucleic acid sample will be a tissue or cell sample prepared for standard in situ hybridization methods described below. The sample is prepared such that individual chromosomes remain substantially intact prepared according to standard techniques. Alternatively, the nucleic acid may be isolated, cloned or amplified. It may be, e.g., genomic DNA, mRNA, or cDNA from a particular chromosome, or selected sequences (e.g. particular promoters, genes, amplification or restriction fragments, cDNA, etc.) within particular amplicons or deletions disclosed here.

The nucleic acid sample may be extracted from particular cells or tissues, e.g. melanocytes. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The sample may be isolated nucleic acids immobilized on a solid.

The term "probe" or "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. The probes of the present invention are produced from nucleic acids found in the regions described herein. The probe or genomic nucleic acid sample may be processed in some manner, e.g., by blocking or removal of repetitive nucleic acids or enrichment with unique nucleic acids. The word "sample" may be used herein to refer not only to detected nucleic acids, but to the detectable nucleic acids in the form in which they are applied to the target, e.g., with the blocking nucleic acids, etc. The blocking nucleic acid may also be referred to separately. What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767–773; Johnston (1998) *Curr. Biol.* 8: R171-R174; Schummer (1997) *Biotechniques* 23: 1087–1092; Kern (1997) *Biotechniques* 23: 120–124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

"Providing a nucleic acid sample" means to obtain a biological sample for use in the methods described in this invention. Most often, this will be done by removing a sample of cells from an animal, but can also be accomplished by using previously isolated cells (e.g. isolated by another person), or by performing the methods of the invention in vivo.

"Tissue biopsy" refers to the removal of a biological sample for diagnostic analysis. In a patient with cancer, tissue may be removed from a tumor, allowing the analysis of cells within the tumor.

DESCRIPTION OF THE SPECIFIC EMBODIMENTS

Introduction

The present invention provides for unique and accurate methods for distinguishing benign melanocytic nevi, such as Spitz nevi, from malignant melanoma.

This invention is based upon the observation that chromosomal regions that have frequently altered copy numbers in melanoma such as 1q, 6p, 7p, 9p, or 10q, are rarely changed in Spitz nevi. In addition, Spitz nevi cells show a single amplification of chromosomal region 11p, particularly 11p15.5, as shown by the increase of its copy number, a phenomenon that is exceedingly rare in melanoma. This difference in pattern of chromosomal aberrations between Spitz nevi and melanoma can lead to more accurate diagnostic distinction of Spitz nevi from melanoma.

The frequency of chromosomal aberrations among melanoma cells, including primary and metastatic melanoma has been studied using CGH (Bastian et al., Cancer Res 58: 2170–5 (1998). One of the findings of this experiment was the frequent loss of chromosome 9 and chromosome 10 that occurred in 81% and 63% of the tumors, respectively. By comparing the frequency of occurrence in thin and thick tumors, and comparing parts of tumors that were in different phases of tumor progression, it was discovered that losses of chromosomes 9 and 10 occurred early in tumorigenesis.

Another set of experiments was performed, extending the data set to 70 tumors. Results from the second set of experiments confirmed that losses of chromosomes 9 and 10 are the most frequent changes in primary melanomas of the skin.

Figure 1:
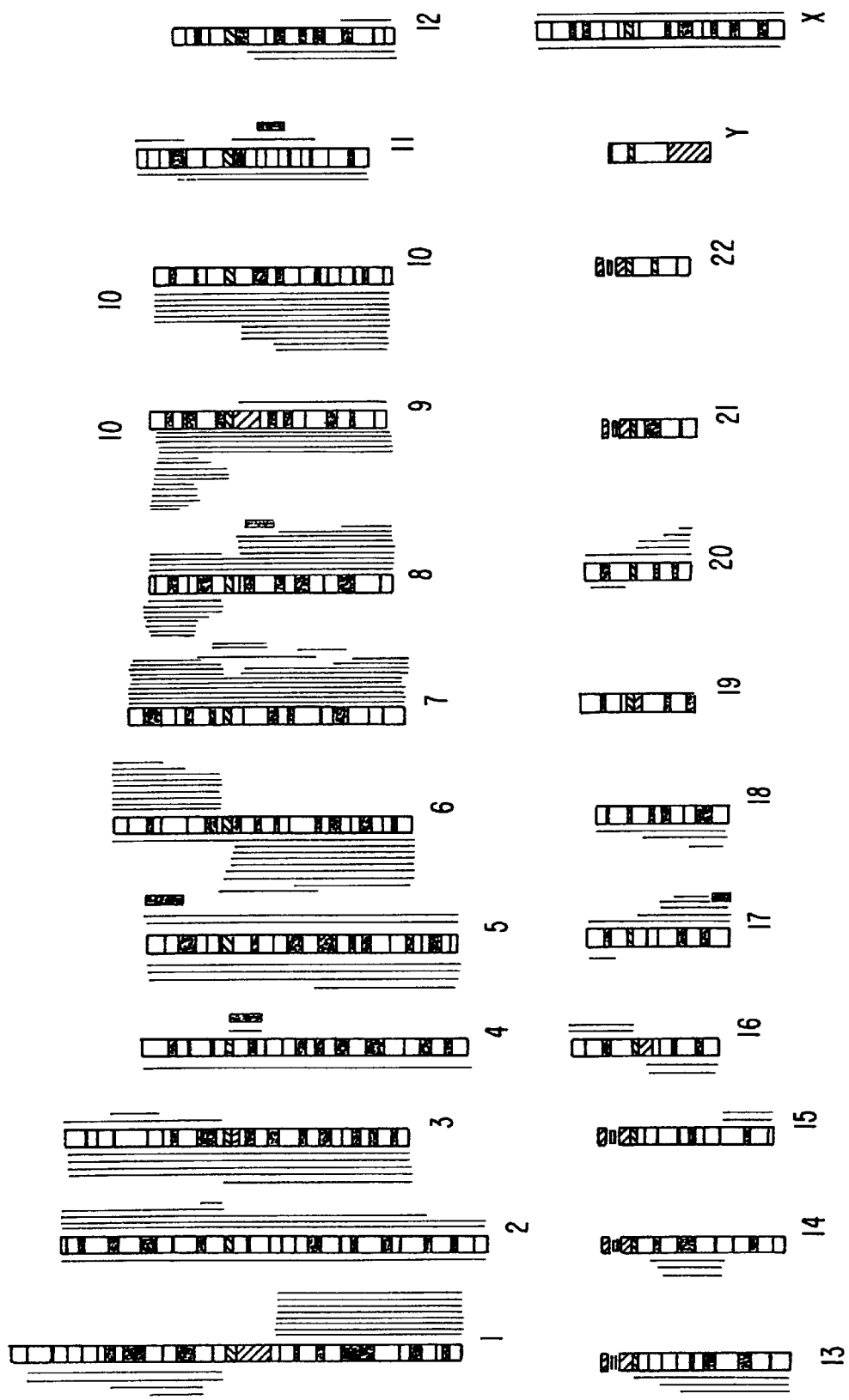
FIG. 1 shows the summary of chromosome copy number changes in 32 primary cutaneous melanomas. Chromosomal gains are shown as lines to the right of the chromosome ideogramms, losses are shown as lines to the left. Thick lines to the right indicate amplifications, thick lines to the left summarize losses in 10 cases (Bastian et al., Cancer Res 58: 2170–5, 1998).

In these 70 melanomas only four exhibited no changes by CGH. Results of these experiments performed with melanoma cells are shown in FIG. 1.

General Methods for Measuring Chromosomal Abnormality

Genomic instability is a hallmark of solid tumors, and virtually no solid tumor exists which does not show major alterations of the genome. With the vast majority of tumors this instability is expressed at the level of the chromosomal complement, and thus is detectable by cytogenetic approaches (Mitelman, F., Catalog of chromosome aberrations in cancer, 5th Edition (New York: Wiley-Liss) (1994)). However, aneuploidy per se is not indicative of malignancy and many benign tumors can have an aberrant karyotype (Mitelman, 1994). To efficiently take advantage of aneuploidy as a marker, it is mandatory to know characteristic aberrations of the tumors that are to be differentiated.

There have been several studies of ploidy in Spitz nevi using measurement of nuclear DNA content by image cytometry or flow cytometry (Howat et al., Cancer 63, 474–8 (1989); LeBoit et al., J Invest Dermatol 88, 753–7 (1987); Otsuka et al., Clin Exp Dermatol 18, 421–4 (1993); Vogt et al., Am J Dermatopathol 18, 142–50 (1996)). However, routine application of these techniques has been hampered by the complexity of the procedure and more importantly by its lack of sensitivity.

Several techniques that permit the study of chromosomal complement in post-fixation tissue have been developed. Fluorescence in-situ hybridization (FISH) can be used to study copy numbers of individual genetic loci in interphase nuclei (Pinkel et al., Proc. Natl. Acad. Sci. U.S.A. 85, 9138–42 (1988)) and comparative genomic hybridization (CGH) (Kallioniemi et al. Science 258, 818–2 1 (1992)) has proven a useful technique (Houldsworth et al. Am J Pathol 145, 1253–60 (1994)) to probe the entire genome for copy number changes of chromosomal regions.

The application of FISH as an adjunctive diagnostic technique for the differentiation of Spitz nevi from melanomas has been suggested previously (De Wit et al., J Pathol. 173, 227–33 (1994)). The investigators used a centromeric probe for chromosome 1 and found a significant difference in the number of cells with an aberrant number of signals between 15 melanoma and 15 Spitz nevi. At this point no detailed knowledge about chromosomal changes in primary melanomas of the skin was available and chromosome 1 was selected based on its frequent numerical change in melanoma metastasis (Thompson et al., Cancer Genet Cytogenet 83, 93–104 (1995)). It is to be expected that a selection of a panel of chromosomal markers of regions that are frequently involved in primary melanomas could increase sensitivity and specificity to a level that would allow the application of FISH as a routine method. To achieve this goal, it is essential to know the pattern of aberrations in melanomas as well as its benign counterparts.

Detection of Copy Number

Methods of evaluating the copy number of a particular gene or chromosomal region are well known to those of skill in the art. In this invention, the presence or absence of chromosomal gain or loss can be evaluated simply by a determination of copy number of the regions identified here. Typically, the regions evaluated are 1q, 6p, 7p, 9p, 10q, and 11p.

Hybridization-based Assays

Preferred hybridization-based assays include, but are not limited to, traditional "direct probe" methods such as Southern Blots or In Situ Hybridization (e.g., FISH), and "comparative probe" methods such as Comparative Genomic Hybridization (CGH). The methods can be used in a wide variety of formats including, but not limited to substrate (e.g. membrane or glass) bound methods or array-based approaches as described below.

In situ hybridization assays are well known (e.g., Angerer (1987) Meth. Enzymol 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

In Comparative Genomic Hybridization methods a first collection of (sample) nucleic acids (e.g. from a possible tumor) is labeled with a first label, while a second collection of (control) nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227–1234; Pinkel (1988) *Proc. Natl. Acad. Sci. USA* 85: 9138–9142; EPO Pub. No. 430,402; *Methods in Molecular Biology, Vol. 33: In Situ Hybridization Protocols*, Choo, ed., Humana Press, Totowa, N.J. (1994), etc. In one particularly preferred embodiment, the hybridization protocol of Pinkel et al. (1998) *Nature Genetics* 20: 207–211 or of Kallioniemi (1992) *Proc. Natl Acad Sci USA* 89:5321–5325 (1992) is used.

The methods of this invention are particularly well suited to array-based hybridization formats. For a description of one preferred array-based hybridization system see Pinkel et al. (1998) *Nature Genetics*, 20: 207–211.

Arrays are a multiplicity of different "probe" or "target" nucleic acids (or other compounds) attached to one or more surfaces (e.g., solid, membrane, or gel). In a preferred embodiment, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606–614; Jackson (1996) *Nature Biotechnology* 14:1685; Chee (1995) *Science* 274: 610; WO 96/17958.

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting approach has been automated to produce high density spotted arrays (see, e.g., U.S. Pat. No: 5,807,522). This patent describes the use of an automated systems that taps a microcapillary against a surface to deposit a small volume of a biological sample. The process is repeated to generate high density arrays. Arrays can also be produced using oligonucleotide synthesis technology. Thus, for example, U.S. Pat. No. 5,143,854 and PCT patent publication Nos. WO 90/15070 and 92/10092 teach the use of light-directed combinatorial synthesis of high density oligonucleotide arrays.

In another embodiment the array., particularly a spotted array, can include genomic DNA, e.g overlapping clones that provide a high resolution scan of the amplicon corresponding to the region of interest. Amplicon nucleic acid can be obtained from, e.g., MACs, YACs, BACs, PACs, P1s, cosmids, plasmids, inter-Alu PCR products of genomic clones, restriction digests of genomic clone, cDNA clones, amplification (e.g., PCR) products, and the like.

In various embodiments, the array nucleic acids are derived from previously mapped libraries of clones spanning or including the target sequences of the invention, as well as clones from other areas of the genome, as described below. The arrays can be hybridized with a single population of sample nucleic acid or can be used with two differentially labeled collections (as with an test sample and a reference sample).

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.*, 164: 336–344; Kremsky (1987) *Nucl. Acids Res.* 15: 2891–2910). Modified nucleotides can be placed on the target using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known.

Target elements of various sizes, ranging from 1 mm diameter down to 1 $\mu$m can be used. Smaller target elements containing low amounts of concentrated, fixed probe DNA are used for high complexity comparative hybridizations since the total amount of sample available for binding to each target element will be limited. Thus it is advantageous to have small array target elements that contain a small amount of concentrated probe DNA so that the signal that is obtained is highly localized and bright. Such small array target elements are typically used in arrays with densities greater than $10^4/cm^2$. Relatively simple approaches capable of quantitative fluorescent imaging of 1 $cm^2$ areas have been described that permit acquisition of data from a large number of target elements in a single image (see, e.g., Wittrup, *Cytometry* 16: 206–213, 1994).

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait (1984) Oligonucleotide Synthesis: A Practical Approach, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122–1126). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, probe nucleic acid is spotted onto a surface (e.g., a glass or quartz surface). The nucleic acid is dissolved in a mixture of dimethylsulfoxide (DMSO) and nitrocellulose and spotted onto aminosilane coated glass slides. Small capillaries tubes can be used to "spot" the probe mixture.

A variety of other nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25 X SSPE-T at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., cot-1 DNA). The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, VoL 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105–114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Probes useful in the methods described here are available from a number of sources. For instance, P1 clones are available from the DuPont P1 library (Shepard, et al., *Proc. Natl. Acad. Sci. USA*, 92: 2629 (1994), and available commercially from Genome Systems. Various libraries spanning entire chromosomes are also available commercially (Clonetech, South San Francisco, Calif.), or from the Los Alamos National Laboratory.

Labeling and Detection of Nucleic Acids

In a preferred embodiment, the hybridized nucleic acids are detected by detecting one or more labels attached to the sample or probe nucleic acids. The labels may be incorporated by any of a number of means well known to those of skill in the art. Means of attaching labels to nucleic acids include, for example nick translation or end-labeling (e.g with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g, horse radish peroxidase, alkaline phosphatase and others commonly used in an ELISA), and calorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye can differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. The nucleic acid probe may also be labeled with digoxigenin and then detected with an antibody that is labeled with a fluorochrom, or an enzyme such as horseradish peroxidase or alkaline phosphatase. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe-CdS core-shell nanocrystals enclosed in a silica shell can be easily derivatized for coupling to a biological molecule (Bruchez et al. (1998) *Science*, 281: 2013–2016). Similarly, highly fluorescent quantum dots (zinc sulfide-capped cadmium selenide) have been covalently coupled to biomolecules for use in ultrasensitive biological detection (Warren and Nie (1998) *Science*, 281: 2016–2018).

Amplification-based Assays

In another embodiment, amplification-based assays can be used to measure copy number. In such amplification-based assays, the nucleic acid sequences act as a template in an amplification reaction (e.g Polymerase Chain Reaction (PCR). In a quantitative amplification, the amount of amplification product will be proportional to the amount of template in the original sample. Comparison to appropriate (e.g. healthy tissue) controls provides a measure of the copy number of the desired target nucleic acid sequence. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.).

Other suitable amplification methods include, but are not limited to ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), and self-sustained sequence replication (Guatelli et al. (1990) *Proc. Nat. Acad. Sci. USA* 87: 1874).

Detection of Gene Expression

As indicated below, a number of oncogenes are found in the regions of amplification disclosed here. Thus, oncogene activity can be detected by, for instance, measuring levels of the gene transcript (e.g. mRNA), or by measuring the quantity of translated protein.

Detection of Gene Transcripts

Methods of detecting and/or quantifying t gene transcripts using nucleic acid hybridization techniques are known to those of skill in the art (see Sambrook et al. supra). For example , a Northern transfer may be used for the detection of the desired mRNA directly. In brief, the niRNA is isolated from a given cell sample using, for example, an acid guanidinium-phenol-chloroform extraction method. The mRNA is then electrophoresed to separate the mRNA species and the MRNA is transferred from the gel to a nitrocellulose membrane. As with the Southern blots, labeled probes are used to identify and/or quantify the target mRNA. In another preferred embodiment, the gene transcript can be measured using amplification (e.g. PCR) based methods as described above for directly assessing copy number of the target sequences.

Detection of Expressed Protein

The "activity" of the target oncogene can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

Kits for Use in Diagnostic and/or Prognostic Applications

For use in diagnostic, research ,and therapeutic applications suggested above, kits are also provided by the invention. In the diagnostic and research applications such kits may include any or all of the following: assay reagents, buffers, nucleic acids for detecting the target sequences and other hybridization probes and/or primers. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example One

CGH and FISH studies of Spitz nevi cells

This example demonstrates that using CGH studies, Spitz nevi cells are shown to have a gain in chromosomal region 11. Seventeen (17) cases of Spitz nevi were studied using CGH. The procedures of CGH were performed following standard protocols as described as follows.

Material and Methods
Tumor Material

Formalin-fixed, paraffin-embedded tissue from Spitz nevi from 17 patients were retrieved from the archives of the Department of Dermatology (University Hospital, Würzburg, Germany) and the Dermatopathology Section, Departments of Pathology and Dermatology (University of California, San Francisco). We selected lesions that had an extensive and densely cellular dermal component that allowed the collection of mostly melanocytes and had at most a sparse lymphocytic infiltrate, so that lymphocyte DNA would not obscure aberrations in the neoplastic cells.
DNA Preparation Paraffin material: 30 µm sections were cut, with a 5 µm section for H & E every 5 sections. The unstained 30 µm sections were placed on glass slides and an area of interest was microdissected without de-paraffinizing.

Microdissection was carried out manually under a dissecting microscope. Depending on the size of the tumor 20–60 unstained sections were used and regions with a high density of tumor cells were separated from normal cells. The dissected tumor parts were collected in tubes and de-paraffinized by washing with xylene and ethanol. DNA extraction and labeling was performed as published by Isola et al. (8). Briefly, tissue was incubated until complete digestion (3 days) with proteinase K (Life Technologies, Inc., Gaithersburg, Md.) in a 50 mM Tris pH8.5, 1 mM EDTA, 0.5% Tween 20 buffer. DNA was extracted with phenol-chloroform-isoamylalcohol (25:24:1, v/v), precipitated with 7.5 M ammonium acetate and 100% ethanol, and resuspended in water. The amount of DNA obtained ranged from 2 to 12 µg.
Comparative Genomic Hybridization (CGH) and Digital Image Analysis All tumors were measured both with the tumor DNA labeled with fluorescein-12-dUTP (DuPont, Inc., Boston, Mass.), and reference DNA with Texas red-5-dUTP ("standard" labeling), and with the labeling reversed. Labeling was performed by Nick translation. Nick translation conditions were adjusted so that the mean probe fragment size after labeling ranged between 800 and 1500 bp. The hybridization mixture consisted of 200–1000 ng of labeled tumor DNA, 200 ng inversely labeled sex-matched normal human reference DNA from peripheral blood lymphocytes, and 25 µg human Cot-1 DNA (Life Technologies, Inc., Gaithersburg, Md.) dissolved in 10 µl hybridization buffer (50% formamide, 10% dextrane sulfate, and 2×SSC, pH 7.0). Hybridization was carried out for 2–3 days at 37° C. to normal metaphases (9). All samples were investigated with a single batch of metaphase slides. Slides were washed three times in a washing solution (50% formamide in 2×SSC, pH) at 45° C., once in PN buffer (0.1 M $NaH_2PO_4$, 0.1 M $Na_2HPO_4$, and 0.1% Nonidet P40, pH 8.0), and once in distilled water (both 10 minutes at room temperature). Slides were counterstained with 4,6-diamino-2-phenylindole in an anti-fade solution. Hybridization quality was evaluated as published previously (7). Digital images were collected from five metaphases with a Photometrics CCD camera (Microimager 1400, Xillix Technologies, Vancouver, British Columbia, Canada) on a standard fluorescence microscope. The average tumor/reference fluorescence ratios along each chromosome were calculated with custom CGH analysis software. Measurements were made on at least 4 copies of each autosome.
Controls and Threshold Definitions Normal DNA and DNA from tumor cell lines with known aberrations were used as controls. We regarded a region as aberrant when 1) either the standard labeling or the reverse labeling resulted in a tumor:reference fluorescent ratios <0.80 or >1.2 or 2) both the standard and the reverse labeling resulted in a tumor:reference fluorescent ratios <0.85 or >1.15.

Figure 2:
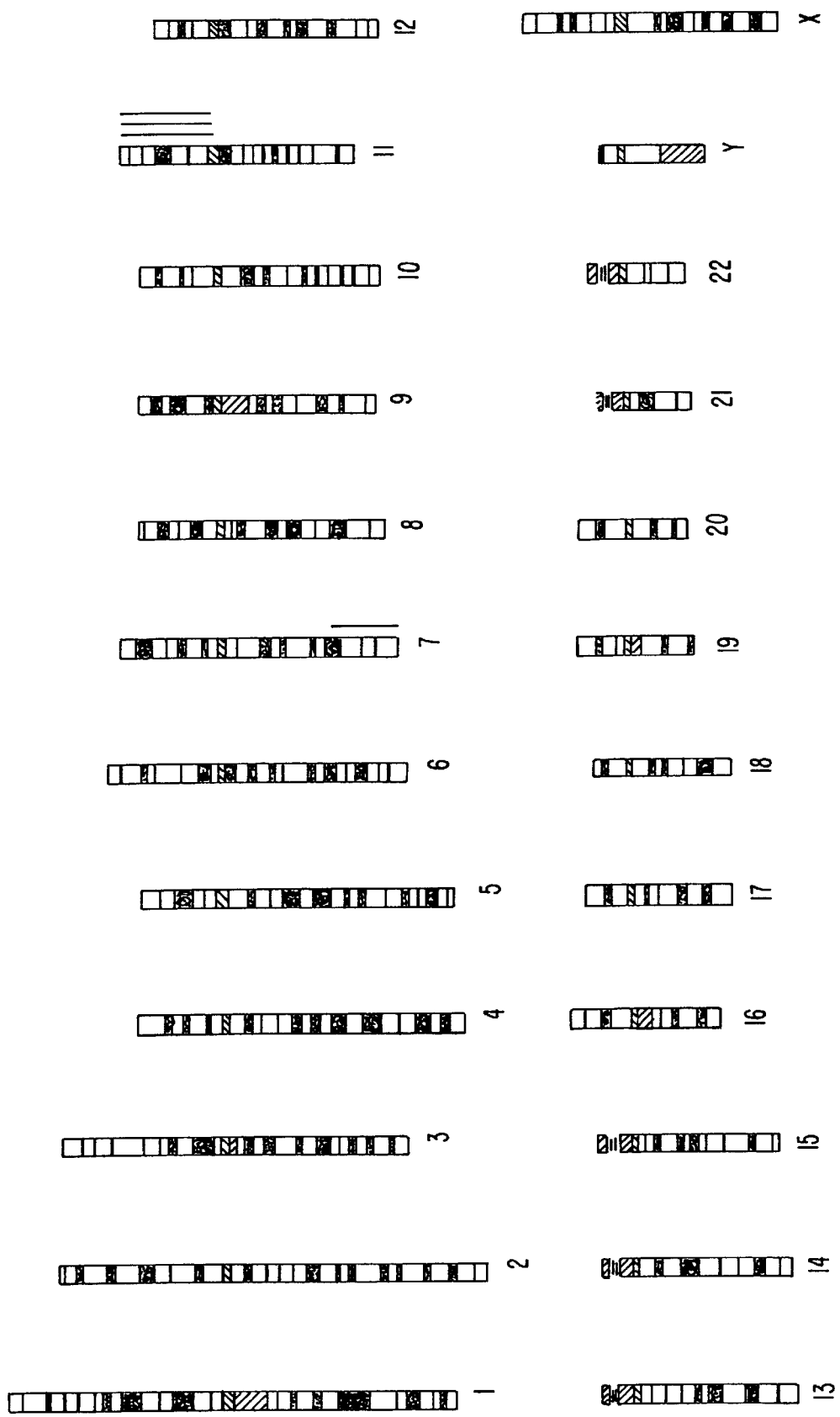
FIG. 2 shows the summary of chromosome copy number changes in 17 Spitz nevi. Chromosomal gains are shown as lines to the right of the chromosome ideogramms. Thick lines indicate amplifications.

Results of this experiment showed that 13 tumors did not show any chromosomal aberrations. One case had an isolated gain of the distal part of chromosome 7, 7q21-qter. Three cases showed a single high level gain of the entire short arm of chromosome 11 (FIG. 2). This phenomenon of a gain in chromosome 11p of Spitz nevi cells is not seen among melanoma cells, as shown in FIG. 1.
Fluorescence In-Situ Hybridization (FISH)

Dual-color FISH was carried out on tissue sections of the cases in which tissue was left after CGH (14/17). Probes mapping to the short arm (RMC11B022 and RMC11P014) and the long arm (RMC11P008) of chromosome 11 were obtained from the resource of the laboratory. Probes were labeled by nick translation with Cy3 (Amersham, Arlington Heights, Ill.) or Digoxigenin (Boehringer Mannheim, Indianapolis Ind.). 6 µm sections were mounted on positively charged glass slides (Fisher Scientific, Pittsburgh, Pa.), deparaffinized, and hydrated by decreasing strength ethanol. Sections were incubated for 2–4 min in 1 M sodium thiocyanate at 80° C., in 4 mg/ml Pepsin in 0.2 N HCl at 37° C. for 4–8 min, dehydrated by increasing strength ethanol and air-dried. Slides were denatured in 70% formamide, 2×SSC pH 7.0 for 5 min at 72° C., and dehydrated again in a graded ethanol series. 2.5 to 25 ng of each of the labeled probes together with 20 µg Cot-1 DNA (Life Technologies, Inc., Gaithersburg, Md.) were dissolved in 10 µm hybridization buffer (50% formamide, 10% dextrane sulfate, and 2 ×SSC, pH 7.0) and denatured for 10 min at 72° C. Hybridization was carried out for 48–72 hours at 37° C. Slides were washed three times in washing solution (50% formamide in 2 ×SSC, pH 7.0) at 45° C., once in 2×SSC at room temperature (RT), and once in 0.1% Triton X100 in 4×SSC/ at RT. Subsequently, sections were incubated with 10% BSA in 4×SSC in a moist chamber at 37° C., and then with a FITC labeled anti-digoxigenin antibody (Boehringer Mannheim, Indianapolis Ind.) diluted in 4×SSC with 10% BSA. Sections were counterstained with 4,6-diamino-2-phenylindole (Sigma, St. Louis, Miss.) in an anti-fade solution. The two-tailed student's t-test was used for the comparison of FISH signals for the locus of interest and the reference probe.

Results

Figure 3:
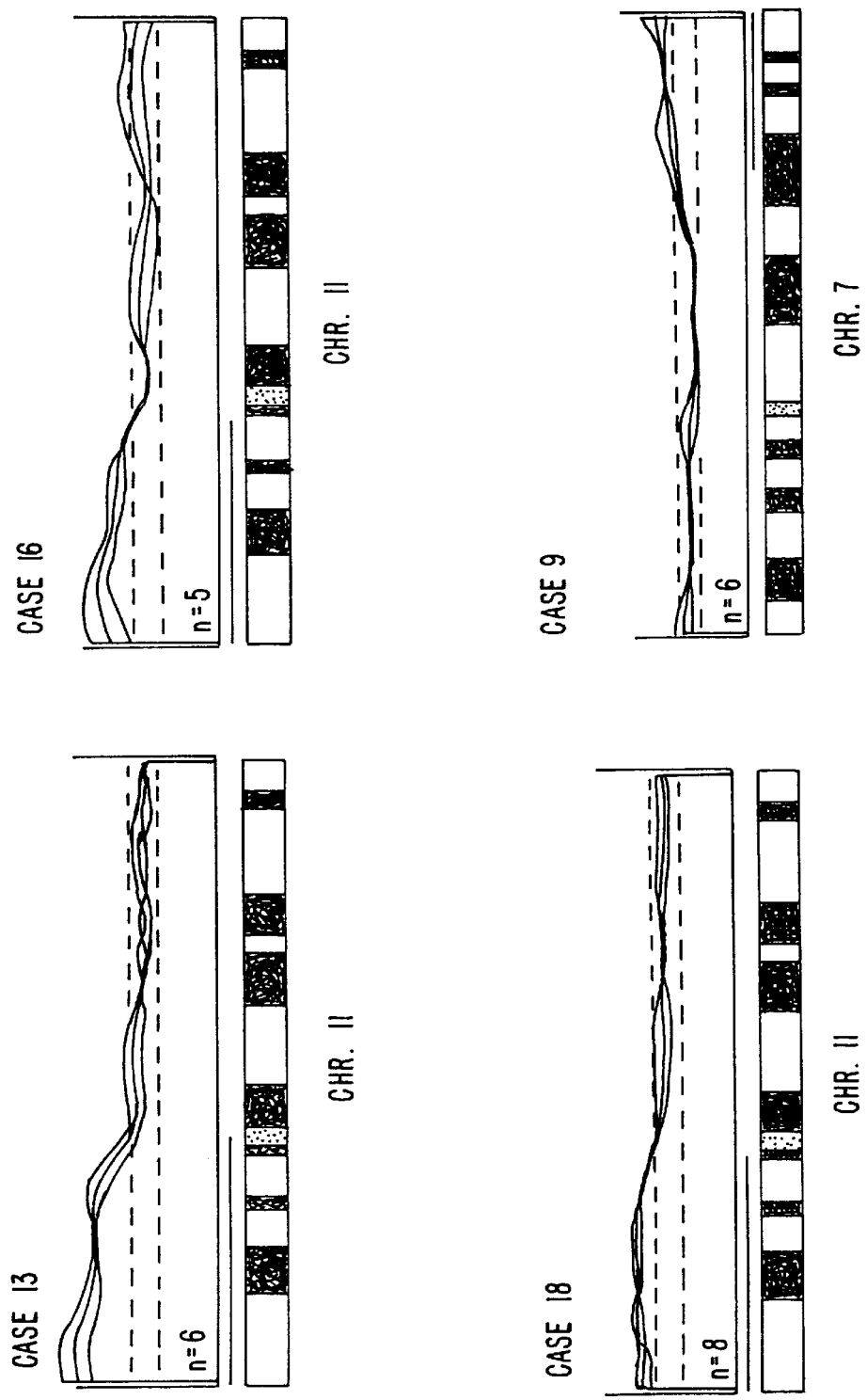
FIG. 3 shows the average ratio profiles of fluorescence intensity of tumor vs. reference DNA in the four Spitz nevi that had abnormal CGH profiles. The dotted lines indicate the 1.2 and 0.8 ratio thresholds that were used for defining aberrations. n indicates the number of chromosomes measured for the respective profile.

Table 1 shows the clinical information of the Spitz nevi patients, and aberrations found by CGH and FISH. Patient age ranged from 3–45 years (mean 18 years). Follow-up was available from most patients. The follow-up time was 1.2–9 years (mean 4.9 years). All patients with available follow-up were free of disease by the end of the follow-up interval. In one case (case 16) 2 recurrences prior to the final excision of the lesion that entered the study occurred, possibly because the tumor was curetted twice. Recut sections of all cases represented typical Spitz nevi by histopathological examination. 13 of the 17 tumors (76%) showed no DNA copy number changes by CGH. Three cases (18%) showed gain of the entire short arm of chromosome 11 as the sole abnormality. (FIG. 3). One case showed gain of chromosome 7q21-qter as the only abnormality (FIG. 3).

Figure 4:
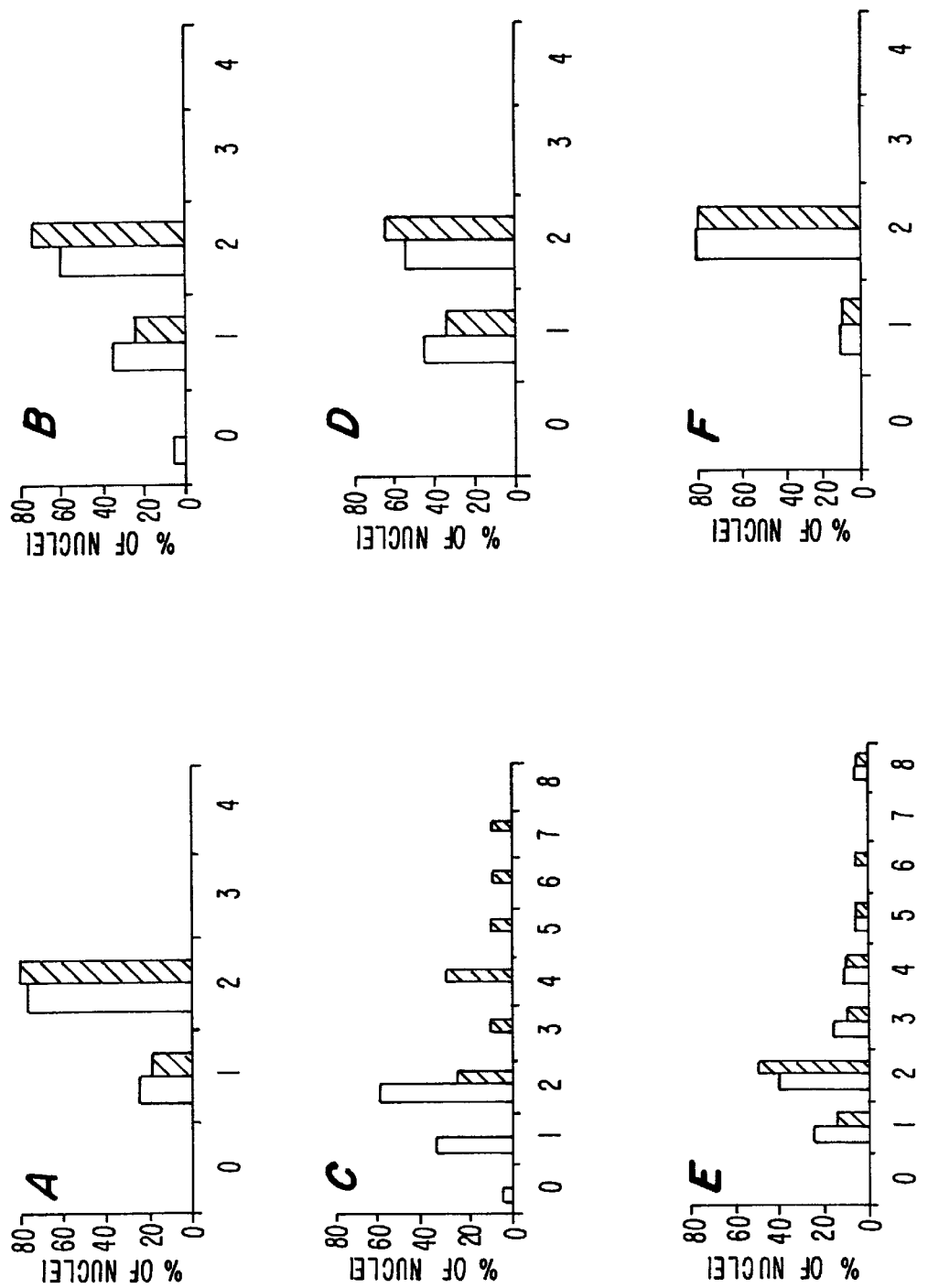
FIG. 4A–4F shows the frequency distribution of hybridization signals after dual-target hybridization of probe RMC11B022 for chromosome 11p (black bars) and RMC11P008 for chromosome 11q (white bars). Three cases of Spitz nevi are shown. Case 2(A, B) showed no chromosomal aberrations by CGH, Case 13(C, D) had an gain of chromosome 11p by CGH, Case 15(E, F) did not show aberrations by CGH, it had a subpopulation of tumor cells with large nuclei. Charts A, C, E show signal distribution in tumor cells; Charts B, D, F show signal distribution in keratinocytes of the corresponding lesions.

FISH measurements were performed to tissue sections in order to study the histopathologic distribution of the recurrent gain on chromosome 11p and to find potential minor populations of cells with this aberration in the cases with normal CGH profiles. A test probe was selected that mapped to the distal part of chromosome 11p (11p15.5, clone RMC11B022) and a reference probe mapping to chromosome 11q23 (clone RMC11P008). In all experiments keratinocytes of the epidermis adjacent to the lesion were used as internal controls. As the hybridization was carried out on sections of 6 µm thickness, many nuclei were not fully represented in the slide. For counting hybridization signals, we selected nuclei that appeared minimally truncated when the focus of the microscope was slightly altered. The nuclear signal counts in keratinocytes for the q-arm and the p-arm probe ranged from mean values of 1.6–1.9 and 1.7–1.9, respectively (FIGS. 4b, 4d, 4f). A mean of 2.0 is expected if all counted nuclei are intact and the hybridization efficiency is 100%. The numbers of p-arm signals tended to be slightly higher than that of the q-arm, which can be explained by the larger size of the p-arm probe, resulting in slightly higher hybridization efficiencies.

However, this difference was not statistically significant. As the variance of the signal number was low (0.16–0.24) in this control population of supposedly normal cells, counting 20 cells per tumor was sufficient to establish the success of the hybridization. When analyzing the neoplastic cells, 20 cells of each morphologically distinct subpopulation were counted. The three cases that had a gain of chromosome 11p by CGH showed a mean of 3.5–5.3 signals with the p-arm probe compared to a mean of 1.5–2.1 counts for the q-arm probe (FIG. 4c,). This difference was highly significant (p<0.00001). The counts for the q-arm (control) probes were not statistically different from signal counts in keratinocytes (normal cells) of the respective lesions. The ratio of p-arm signals to q-arm signals in the cases with increased copies of chromosome 11p ranged from 1.8–3.0. The increased signal number of the p-arm probe was present in virtually every cell of each the nevi. From the 14 tumors that had no gain of chromosome 11p by CGH twelve could be studied by FISH. In the other two cases the paraffin blocks were exhausted. Of these twelve cases, eleven had no significant differences in signal distribution of the probes for p-arm and the q-ann of chromosome 11 (FIGS. 4a, 4b). One case (case 5) had 2.4 p-arm signals vs. 1.9 q-arm signals, a difference which was statistically significant (p=0.01). In two cases (cases 3 and 15) a subpopulation of cells was present that had increased numbers of both the q-arm and the p-arm signal (FIG. 4e). These cells mostly had considerably larger nuclei than the tumor cells with 1–2 signals, and are thus likely to be polyploid.

As illustrated in FIG. 3, the area of chromosome 11 that was found by CGH to be gained in three cases seems to be identical. The profiles of case 13 and case 16 suggest the highest increase of DNA copy number towards the p-telomere. However, the profiles of the CGH measurement in which the labeling was reversed showed a decrease of red:green fluorescence ratio toward the telomere, indicating that the p-telomeric ratio increase is artifactual. To confirm this, FISH experiments were performed with a different probe for the p-arm that mapped more proximally to 11p14 (RMC11P014). The number of signals in the nuclei of the tumor cells with this probe was similar to that found with the probe for 11p15.

One probe mapped to the distal part of the p-arm of chromosome 11 and the second probe mapped to 11q. Of the three cases that showed a gain of chromosome 11p, 6–10 signals of the 11p probe per nucleus were detected, whereas the probe that mapped to the q-arm only gave two signals. Interestingly, the signal number was virtually constant over the entire lesion, suggesting a clonal nature of the neoplasms. Among the other Spitz nevi studied which showed no indication of 11p gain in CGH, only one additional case showed an amplification of 11p. All other cases had two signals of both markers. Exceptions were cells with large nuclei that occurred in three tumors. Those cells had up to 10 signals of both markers. These findings suggest that gain of chromosome 11p is a recurrent aberration in Spitz nevi. The cells of Spitz nevi are diploid, with the exception of cells with large nuclei that can be polyploid. Spitz nevi are clonal neoplasms.

Table 1: Clinical information of the Spitz nevi and aberrations found by CGH and FISH. (PSCT=pigmented spindle cell tumor, FOD=free of disease, NA=not available).

TABLE 1

| Case | Sex | Age | Aberrations | Clinical Information | Site | Histology | Follow-up |
|---|---|---|---|---|---|---|---|
| S1 | f | 17.9 | none | Since one year slowly enlarging 1.1 × 1.4 cm reddish papule with brown rim | Shin | compound with desmoplasia | FOD, 5.4 y |
| S2 | m | 31.0 | none | Since one unchanged cherry pit-sized dome-shaped reddish nodule | Lower arm | dermal with desmoplasia | FOD, 3.4 y |
| S3 | f | 21.5 | none | NA | Upper back | compound | FOD, 1.2 y |
| S4 | f | 7.2 | none | Since one year cherry-pit-sized tumor | Knee | dermal with desmoplasia | FOD, 4.0 y |
| S5 | f | 23.8 | Amp. 11p (FISH) | Since one year discretely enlarging | Knee | compound | FOD, 7.5 y |

TABLE 1-continued

| Case | Sex | Age | Aberrations | Clinical Information | Site | Histology | Follow-up |
|---|---|---|---|---|---|---|---|
| S6 | m | 7.4 | none | Since 3 month slowly growing lentil-sized, slightly keratotic, elevated | Ear helix | compound with desmoplasia | FOD, 9.3 y |
| S7 | m | 13.7 | none | Since years 1.5 cm, raised, firm nodule | Lateral abdomen | compound | FOD, 2.6 y |
| S8 | f | 3.2 | none | Since 1.5 years growth of a pigmented tumor | Cheek | PSCT | FOD, 6.9 y |
| S9 | f | 31.3 | none | NA | Thigh | compound | FOD, 2.3 y |
| S11 | f | 3.0 | Gain of 7q31-qter | NA | Inner thigh | PSCT | FOD, 8.1 y |
| S12 | f | 23.0 | none | NA | Epigastrium | PSCT | FOD, 4.2 y |
| S13 | f | 45.8 | Amp. of 11p | NA | Thorax | dermal with desmoplasia | FOD, 5.3 y |
| S14 | f | 10.8 | none | since 7 months itching, reddish papule | Cheek | compound | NA |
| S15 | f | 26.7 | none | NA | Shin | dermal | FOD, 1.2 y |
| S16 | f | 23.2 | Amp. of 11p | 1.5 years ago curettage of a lesion that arose 4 months earlier. Lesion recurred one month later and was again curetted. Recurred again after 2 months and was excised. Now, after 2 months, again recurring. Reddish, sharply circumscribed lentil-sized papule. | Tip of nose | compound with scar tissue | FOD, 7.3 y |
| S17 | m | 12.5 | none | NA | Mid back | compound | NA |
| S18 | m | 11.3 | Amp. of 11p | enlarging skin lesion for three month | Calf | compound with desmoplasia | NA |

Discussion

These results show that the majority of Spitz nevi have a normal chromosomal complement, but that a subset may have abnormalities. We detected gains of chromosome 11p in 4/17 cases. Thus Spitz nevi is one of the many benign lesions that contain genetic abnormalities at the chromosomal level. The pattern of chromosomal aberrations in Spitz nevi shows clear differences from that observed in primary cutaneous melanoma. In the latter only a small minority of cases does show no aberrations when analyzed by CGH. In this example, CGH measurements were performed on 102 melanomas and only 5 cases did not show changes. The 5 cases without detectable aberrations had considerable contamination of normal cells in the tumor that may account for at least a part for these findings. In the Spitz nevi of the present study cases with an inflammatory component were excluded, so that contamination of normal cells could not have accounted for the high frequency of negative findings.

The finding of an increased copy number of chromosome 11p in four out of 17 lesions indicates that this aberration represents a recurrent change in Spitz nevi. It suggests that increased dosage of genes of chromosome 11p has relevance in the pathogenesis of this tumor. As the gained genomic fragment is large, additional studies are warranted to refine the extent of the region as a first step toward identifying the critical gene(s). It may well be that in the Spitz nevi without 11p gain, those genes, or the pathways they belong to, are activated by a different mechanism than increase of gene copy number.

A gain of chromosome 11p was not seen in any of the 102 primary melanomas we have analyzed by CGH. Gains including 11p were found in only two cases of the 239 published karyotypes, mostly from metastatic melanomas (11, 12). However, in these two cases the gain extended far on to the q-arm (12).

Furthermore, none of the most frequent findings in primary melanomas, losses of chromosomes 9 and 10, was found in any of the Spitz nevi. However, chromosome 7 was gained in 50% of our melanoma cases (7), and one of the Spitz nevi showed a gain of chromosome 7q23-pter. Thus, even though future studies will be required to determine the full spectrum and frequency of aberrations in Spitz nevi, the current data clearly shows that there is a clear difference in the pattern of chromosomal gains and losses in melanoma and Spitz nevi. These differences raise the possibility of defining genetic markers that can be used for diagnostic purposes. Cytogenetic studies have been of great help in the classification of soft tissue tumors and can provide pivotal diagnostic information (13). A diagnostic test for spitzoid melanocytic neoplasms might include copy number detection of chromosomes 11p 9, and 10. Gains of chromosome 11p could be interpreted as in favor of Spitz nevus, and losses of chromosomes 9 and/or 10 as in favor of melanoma.

It is indeed remarkable that the chromosomal alterations most frequently found in primary melanomas are absent in Spitz nevi. And this absence of aberrations frequently found in melanoma may be a difference that may indeed offer diagnostic opportunities. Previous CGH studies on 32 primary melanomas showed losses of chromosome 9p in 82%, chromosome 10 in 63%, and 6q in 28% of the cases (Bastian et al. 1998). Frequent gains in melanoma involved chromosome 7p (50%), 8q (34%), and 6p (28%). None of these changes was found in our series of Spitz nevi. Note that one study found interstitial deletions of chromosome 9p in two out of 27 Spitz nevi indicating that losses of 9p are not exclusive to melanoma (Healy E, et al., ALLELOTYPES OF PRIMARY CUTANEOUS MELANOMA AND BENIGN MELANOCYTIC NEVI, Cancer Res 56: 589, 1996). It may thus be that the determination of copy number of other chromosomal regions such as 1q, 6p, 7p, and 10q, may prove to be more helpful in the differential diagnosis. The efficacy of such a test needs to be evaluated through the analysis of a larger set of tumors with the inclusion of cases that have conflicting histopathologic criteria but have known follow-up. This will permit determination of the sensitivity and specificity under clinically relevant conditions.

FISH measurements not only confirmed the CGH findings but also allowed some interesting insight into the ploidy and clonality of Spitz nevi. Since almost all cells in the nevi had 2 copies of the control locus on 11q by FISH and CGH showed no aberrant copy numbers for that locus, the large majority of the cells in these nevi are diploid, which is consistent with previous flow cytometry studies (10). Two cases had a subpopulation of cells with large nuclei. Those cells elevated copy number had elevated FISH signals for the two loci tested, indicating that the increased nuclear size is most likely due to polyploidy. These data also show that Spitz nevi are probably comprised of a monoclonal population of melanocytes. This can be concluded from the three cases with a gained 11p, because the increased copy number of this chromosomal arm was present in all cells of the lesions.

In summary, this example shows that in Spitz nevi, (I) the majority of cases have a normal chromosomal complement at the level of CGH resolution, (II) gains of chromosome 11p represent a recurrent aberration in a subset of lesions, (III) Spitz nevi are probably clonal neoplasms, (IV) the majority of the melanocytes of a Spitz nevus are diploid with the exception of cells with large nuclei which can be polyploid, and (V) the clear differences in the location and frequencies of the cytogenetically detectable aberrations in primary cutaneous melanoma and Spitz nevi make CGH and FISH promising techniques for refining diagnostic accuracy of this difficult differential diagnosis.

Example Two

FISH Study of Melanocytic Tumor Using Chromosome 9 Probes

This example demonstrates FISH experiments using chromosome 9 probes in detecting primary melanoma cells.

PI-clones for chromosome 9 were similarly used for FISH studies of sections of primary melanomas. Loss of chromosome 9 was the most frequent finding in the CGH-study of melanoma. The FISH experiments showed that in most cases of melanoma 0–1 signals per nucleus with a probe for chromosome 9p was detected, whereas a simultaneously hybridized reference locus revealed more than 2 signals per nucleus. This indicates that FISH is capable of detecting homozygous and heterozygous deletions in tissue sections.

The selection of hybridization probes will thus be based on the following criteria: (a) the corresponding chromosomal regions should show frequent aberration in one neoplasm and not in the other (e.g. 1q, 6p, 7p, 9p, 10q, and 11p), (b) probes should give strong and reproducible hybridization signals.

Example Three

Tissue Hybridization Protocols

This example demonstrates the use of tissue hybridization protocols in studying the difference in signal ratios per chromosome locus between melanoma cells and Spitz nevi cells.

A hybridization protocol is adapted from Thompson et al., *Cancer Genet Cytogenet* 83, 93–104 (1995). Briefly, tissue sections are mounted on positively charged slides. The slides are heated at 55° C. for about 30 minutes and deparaffinized with xylene, and ethanol dehydrated. They are then sequentially incubated in NaSCN, followed by Pepsin. After being denatured in formamide, they are hybridized using standard techniques. Probes will be labeled directly with Cy-3 and indirectly with digoxigenin that will later be detected with FITC-labeled anti-digoxigenin antibodies. Alternative labeling approaches may be employed so as to be able to detect three differentially labeled probes in one hybridization.

Based on previous studies, it is expected that counting signals of each hybridization probe in a total of 25 tumor cell nuclei and 25 nuclei of normal tissue cells will suffice. One parameter for decision making will be the ratio of average number of signals per locus per tumor cell compared to the average number of signals per locus in normal cells within the tissue (e.g. keratinocytes of the epidermis or epidermal appendages). According to the preliminary studies, the ratio is expected to be less than one for loci frequently lost in melanoma and more than one for loci gained in Spitz nevi.

The second parameter will be the variance of the signal number per tumor cell. Based on previous studies and experience of others, the variance is expected to be significantly higher in malignant tumors than in benign tumors (De Wit et al., *J Pathol* 173, 227–33 (1994)).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of screening for the presence of a Spitz nevus in a skin tumor sample from a patient, the method comprising detecting the presence of an increase of copy number at 11p, in a nucleic acid sample from the skin tumor sample, thereby detecting the presence of the Spitz nevus.

2. The method of claim 1, further comprising detecting an absence of change in copy number at 9p, 1q 6p, 7p, or 10q in the nucleic acid sample.

3. The method of claim 1, wherein the detecting step comprises:

contacting the nucleic acid sample from the skin tumor sample from the patient with a probe which selectively hybridizes to a target polynucleotide sequence on a chromosomal region at 11p, wherein the probe is contacted with the sample under conditions in which the probe binds selectively with the target polynucleotide sequence to form a stable hybridization complex;

detecting the formation of the hybridization complex; and detecting the presence of an increase of copy number at 11p, thereby detecting the presence of the Spitz nevus.

4. The method of claim 1, wherein the nucleic acid sample is an interphase nucleus.

5. The method of claim 3, wherein the probe is labeled with a detectable composition.

6. The method of claim 5, wherein the detectable composition is selected from the group consisting of a direct label and an indirect label.

7. The method of claim 6, wherein the direct label is Cy3.

8. The method of claim 6, wherein the indirect label is selected from a group consisting of a digoxigenin and a biotin.

9. The method of claim 6, wherein the indirect label is detected by a fluorescent dye.

10. The method of claim 9, wherein the fluorescent dye is FITC.

11. The method of claim 3, further comprising contacting the sample with a reference probe that selectively hybridizes to a polynucleotide sequence at a chromosomal region that is different from 11p.

12. The method of claim 11, wherein the reference probe is labeled with a fluorescent label distinguishable from a label on the probe which selectively hybridizes to the target polynucleotide sequence.

13. The method of claim 3, wherein the step of detecting the hybridization complex comprises determining the copy number of the target polynucleotide sequence.

14. The method of claim 3, further comprising a step of blocking the hybridization capacity of repetitive sequences in the probe.

15. The method of claim 14, wherein the step of blocking the hybridization capacity comprises contacting unlabeled blocking nucleic acids comprising repetitive sequences with the sample.

16. The method of claim 15, wherein the unlabeled blocking nucleic acids are Cot-1 DNA.

17. The method of claim 3, wherein the probe is bound to a solid substrate.

18. The method of claim 17, wherein the probe is a member of an array.

* * * * *